United States Patent
Dubois

(10) Patent No.: US 8,927,746 B2
(45) Date of Patent: Jan. 6, 2015

(54) PROCESS FOR SYNTHESIZING OMEGA-FUNCTIONALIZED ACIDS FROM FATTY ACIDS OR FATTY ESTERS

(75) Inventor: Jean-Luc Dubois, Millery (FR)

(73) Assignee: Arkema France, Colombes Cedex (FR)

( * ) Notice: Subject to any disclaimer, the term of this patent is extended or adjusted under 35 U.S.C. 154(b) by 0 days.

(21) Appl. No.: 14/129,675

(22) PCT Filed: Jul. 10, 2012

(86) PCT No.: PCT/FR2012/051627
§ 371 (c)(1),
(2), (4) Date: Dec. 27, 2013

(87) PCT Pub. No.: WO2013/011226
PCT Pub. Date: Jan. 24, 2013

(65) Prior Publication Data
US 2014/0148607 A1    May 29, 2014

(30) Foreign Application Priority Data
Jul. 19, 2011  (FR) ...................................... 11 56526

(51) Int. Cl.
| | | |
|---|---|---|
| *C07B 43/00* | (2006.01) | |
| *C07C 51/36* | (2006.01) | |
| *C07C 51/09* | (2006.01) | |
| *C07C 227/28* | (2006.01) | |
| *C07C 227/16* | (2006.01) | |
| *C07C 253/22* | (2006.01) | |
| *C07C 229/08* | (2006.01) | |
| *C07C 253/30* | (2006.01) | |
| *C07C 51/285* | (2006.01) | |
| *C07C 51/34* | (2006.01) | |
| *C07C 255/07* | (2006.01) | |
| *C07C 51/377* | (2006.01) | |

(52) U.S. Cl.
CPC ............... *C07C 227/28* (2013.01); *C07C 51/09* (2013.01); *C07C 227/16* (2013.01); *C07C 51/36* (2013.01); *C07C 253/22* (2013.01); *C07C 229/08* (2013.01); *C07C 253/30* (2013.01); *C07C 51/285* (2013.01); *C07C 51/34* (2013.01); *C07C 255/07* (2013.01); *C07C 51/377* (2013.01)
USPC ........................... 554/114; 554/141; 554/147

(58) Field of Classification Search
USPC ......................................... 554/114, 141, 147
See application file for complete search history.

(56) References Cited

U.S. PATENT DOCUMENTS 2,813,113 A    11/1957  Goebel et al.

FOREIGN PATENT DOCUMENTS

| GB | 741739 | * 12/1955 |
| GB | 741739 A | 12/1955 |

OTHER PUBLICATIONS

International Search Report for PCT/FR2012/051627; mailed Oct. 10, 2012.

* cited by examiner

*Primary Examiner* — Deborah D Carr
(74) *Attorney, Agent, or Firm* — Smith, Gambrell & Russell LLP

(57) ABSTRACT

The subject matter of the invention is a process for synthesizing ω-functionalized acids of formula R—$(CH_2)_n$—COOH in which R is COOH or $NH_2CH_2$, from a feedstock of natural origin containing hydroxylated fatty acids.

28 Claims, No Drawings

PROCESS FOR SYNTHESIZING OMEGA-FUNCTIONALIZED ACIDS FROM FATTY ACIDS OR FATTY ESTERS

The work which led to this invention received financial support from the European Union in the context of Framework Program 7 (FP7/2007-2013) under the project number No. 241718 EUROBIOREF.

A subject matter of the present invention is a process for the synthesis of ω-functionalized acids of formula R—(CH$_2$)$_n$—COOH in which R represents COOH or NH$_2$CH$_2$ from a feedstock of natural origin comprising hydroxylated fatty acids.

The polyamides industry uses a whole range of monomers, such as long-chain diacids, diamines and ω-amino acids. These polyamides, normally known as Nylon, are characterized by the length of methylene chain (—CH$_2$)$_n$— separating two amide functional groups —CO—NH—. Thus it is that Nylon 6, Nylon 6,6, Nylon 6,10, Nylon 7, Nylon 8, Nylon 9, Nylon 11, Nylon 13, and the like, are known.

These monomers are, for example, manufactured by a chemical synthesis route using in particular, as starting material, C$_2$ to C$_4$ olefins, cycloalkanes or benzene, but also fatty acids generally comprising 18 carbon atoms, resulting from unsaturated natural oils, such as, in particular, soybean oil, corn oil, linseed oil, palm oil, and the like.

Current developments with regard to the environment are resulting in the use of natural starting materials originating from a renewable source being favored in the fields of energy and chemistry. This is the reason why some studies have been taken up to develop, industrially, processes using fatty acids/esters as starting materials for the manufacture of these monomers.

The main studies have related to the synthesis of 9-aminononanoic acid, which is the precursor of Nylon 9, for oleic acid of natural origin. As regards this specific monomer, mention may be made of the work "n-Nylons, Their Synthesis, Structure and Properties", 1997, published by J. Wiley and Sons, Chapter 2.9 of which (pages 381 to 389) is devoted to Nylon 9.

As regards the synthesis of higher monomers, such as, for example, those resulting, on the one hand, in Nylon 11 or in Nylon 13 and, on the other hand, in higher diacids, only a little literature and a fortiori few industrial preparations are found.

They are directed virtually exclusively at the conversion of natural oils (castor oil, olive oil, soybean oil, sunflower oil, palm oil, and the like) comprising unsaturated C$_{18}$ fatty acids, such as oleic acid and ricinoleic acid, *lesquerella* oil comprising C$_{20}$ lesquerolic acid, erucic rapeseed oil, lunaria oil or sea kale oil comprising C$_{22}$ erucic acid.

One of the rare examples of an industrial process using a fatty acid as starting material is that of the manufacture, from the ricinoleic acid extracted from castor oil, of 11-aminoundecanoic acid, which forms the basis of the synthesis of Rilsan 11®. This process is described in the work "Les Procédés de Pétrochimie" [Petrochemical Processes] by A. Chauvel et al., which appeared in Editions Technip (1986). 11-Aminoundecanoic acid is obtained in several stages. The first consists of a methanolysis of castor oil in a basic medium, producing methyl ricinoleate, which is subsequently subjected to a pyrolysis in order to obtain, on the one hand, heptanaldehyde and, on the other hand, methyl undecylenate. The latter is converted to the acid form by hydrolysis. Subsequently, the acid formed is subjected to a hydrobromination to give the ω-brominated acid, which is converted by amination to 11-aminoundecanoic acid.

The use of hydroxylated fatty acids as starting material for the synthesis of amino acids is not very common outside the industrial example mentioned above. However, mention may be made of the patent application FR 2912741 on behalf of the applicant company, which describes the synthesis of 11-aminoundecanoic acid and 12-amino-dodecanoic acid by a process using in particular metathesis.

The most well known saturated diacids (or diesters) are those comprising chains comprising from 4 to 6 carbon atoms, such as succinic acid (C$_4$), glutaric acid (C$_5$), or adipic acid (C$_6$). They are generally synthesized by the chemical route or, more recently, for succinic acid, by the fermentation route.

On the other hand, long-chain diacids are obtained either by fermentation of paraffins or of fatty acids or also by oxidation of cycloalkane, as in the case of the oxidation of cyclododecane to give dodecanedioic acid, or by cracking, in a basic medium, ricinoleic acid to give sebacic acid (C$_{10}$ diacid) or lesquerolic acid to give the C$_{12}$ diacid dodecanedioic acid.

The properties, syntheses and uses of these diacids are described in Ullmann's Encyclopedia, Vol. A8, pages 526-536. The saturated or unsaturated diacids are generally obtained industrially according to the various methods mentioned in this reference. Apart from the syntheses by condensation or fermentation, methods by decomposition, such as, in particular, the ozonolysis, the oxidation or the cracking of optionally hydroxylated unsaturated fatty acids, are encountered (pages 526, 527 and 532 of this publication). In the patent applications published under the numbers FR 2917406 and FR 2921363, the applicant company describes this type of synthesis applied to unsaturated fatty acids.

The use of natural oils as source of unsaturated fatty acids presents a tricky problem insofar as they consist of a mixture of various saturated and unsaturated acids, optionally polyunsaturated acids, which results in the formation, during the treatment, in particular when oxidative cleavage is employed, of multiple by-products due to the presence of multiple unsaturations which require expensive separation/purification treatments. This is true both for the fatty acids and for the hydroxylated fatty acids.

The problem posed by the presence, within the oil, of various unsaturated fatty acids exists with all the more acuteness as, in the future, in order to improve productive outputs, there will be increasing prompting to use GMO plants.

In order to illustrate this phenomenon, mention may be made of the publication by Linnaeus Plant Science (Jack Grushcow, "Optimising Oil Seed Potential for Industrial Application", Renewable Resources and Biorefineries Conference, 6-8 Sep. 2006, The University of York, York, UK, and Jack Grushcow, "Industrial Oil Seed Opportunities", Soy 20-20, September 2004, Annual Meeting) which describes a mechanism of formation of the various hydroxylated fatty acids synthesized in a process using *Arabidopsis thaliana* as model plant. According to this process, oleic acid, the main acid produced, can be converted by hydroxylation into ricinoleic acid, itself converted by dehydrogenation into densipolic acid, the latter two being capable, by "elongation", of respectively forming lesquerolic acid and auricolic acid.

The invention is targeted at overcoming these disadvantages by using, as starting material, a natural oil rich in unsaturated hydroxylated fatty acids which are converted to saturated hydroxylated fatty acids, the latter then being dehydrated to give monounsaturated fatty acids which are optionally converted to nitriles and subsequently subjected to oxidative cleavage, resulting in the ω-functionalized acids, capable of being converted into dinitriles.

In order to simplify the account, the expression "unsaturated hydroxylated fatty acids" would denote the acids whether they are in the acid form, in the ester form or in the polyol ester form, corresponding in practice, in the latter case, to the crude oil.

A subject matter of the present invention is a process for the synthesis of ω-functionalized acids of formula R—$(CH_2)_n$—COOH, in which R represents COOH or $NH_2CH_2$ and n represents an integer between 9 and 12, from a feedstock of natural origin comprising unsaturated hydroxylated fatty acids in the acid, ester (such as methyl) or polyol ester (such as glyceride oil; however, for reasons of ease of reading, reference will be made subsequently to acid to denote equally well acids and esters of alcohols or of polyols) form comprising at least 18 carbon atoms per molecule, comprising the following stages:
a) hydrogenation of the unsaturated hydroxylated fatty acids, resulting in saturated hydroxylated fatty acids,
b) dehydration of the saturated hydroxylated fatty acids, resulting in monounsaturated fatty acids,
c) oxidative cleavage at the double bond of the monounsaturated fatty acids, including unsaturated nitrile derivatives, resulting in an α,ω-bifunctional compound of diacid or nitrile-acid type (or from diacid or nitrile-acid).

The term "acid", in particular "unsaturated hydroxylated fatty acid", as starting material for the process of the invention, for example as defined in the above hydrogenation stage a) and for the continuation of the description, means and includes, systematically, for the continuation (if reference is made to "acid" as starting material), unless more specifically indicated (means and includes), equally well acids and esters of alcohols (such as methyl esters) or esters of polyols (such as glycerol esters, which is the oil) for these fatty acids.

Properly, according to a more specific form of the invention, the starting "acid" material can be in the ester form of said fatty acid.

In the final case of a product which is an α,ω-nitrile-acid compound, according to the process of the present invention, use is made at the start, as starting material for the oxidation reaction, of an unsaturated fatty nitrile prepared, according to a first option, after stage b), by ammoniation (treatment of said fatty acid with ammonia).

According to a second option of the process, said α,ω-nitrile-acid compound can also be prepared from an unsaturated nitrile resulting from the nitrilation of the hydrogenated acid resulting from stage a) carried out at the same time as the dehydration stage b).

Thus, the nitrilation resulting in said unsaturated nitrile, the starting material for the oxidative cleavage of stage c), can be prepared either during a separate stage after the dehydration stage b) or at the same time as the dehydration stage b). Preferably, dehydration and ammoniation are carried out simultaneously.

Generally, for the invention, the term " . . . is between a and b" means, unless otherwise specified, " . . . is between a and b with a and b included" or means the same thing as " . . . varies from a to b").

According to one option of this process, the hydrogenation stage a) is carried out at a temperature of between 70 and 180° C., preferably between 70 and 150° C., more preferably between 90 and 130° C., under an $H_2$ pressure of between 1 and 300 bar, preferably between 5 and 50 bar, in the presence of either homogeneous or heterogeneous hydrogenation catalysts. Said catalysts can be noble metals, such as Pt, Pd or Rh, or transition metals, such as Mo, W, Cr, Fe, Co or Ni, used alone or as a mixture, optionally in the form supported on active charcoal, on alumina and on silica. Mention may be made, among said catalysts, of Raney nickel and/or palladium-on-active charcoal.

The process of the invention can use, as feedstock, either the fatty acid or the fatty ester resulting from the prior hydrolysis or prior alcoholysis of the natural oil, or the crude oil itself. In the latter case, it will be necessary to provide an additional stage of hydrolysis or alcoholysis prior to the oxidative cleavage, in order to separate the glycerol from the reaction medium.

The hydrogenation stage is carried out under operational conditions such that the double bonds present in the feedstock, which simultaneously comprises unsaturated hydroxylated fatty acids and saturated, monounsaturated or polyunsaturated fatty acids, are saturated, while retaining the hydroxyl functional groups present.

According to a specific case, the hydrogenation stage a) is carried out under operational conditions such that the effluent resulting from this hydrogenation stage exhibits an iodine number <5, preferably <3 and more preferably <1 and a hydroxyl number >100 mg KOH/g.

The effluent resulting from this hydrogenation stage will thus exhibit an iodine number (as defined in Vol. A 10, page 214, of Ullmann's Encyclopedia) of less than 5, preferably of less than 3 and more preferably of less than 1 and a hydroxyl number (as defined in Vol. A 10, page 214, of Ullmann's Encyclopedia) of greater than 100 mg KOH/g. The operating conditions will be such that the reduction in the hydroxyl number of the reaction medium at the end of this hydrogenation stage will be ≤10 mg KOH/g.

As regards the stage b) of dehydration of the saturated hydroxylated fatty acids, it is carried out at a temperature of between 100 and 300° C. and in the presence of an acid catalyst, preferably chosen from: sulfuric acid, phosphoric acid, sulfonic acids, alkyl sulfonates or ion-exchange acid resins, such as resins of Amberlyst® type.

As regards the oxidative cleavage stage c), it is carried out using an oxidizing agent chosen from $KMnO_4$, hydrogen peroxide or oxidizing ozone, optionally in combination with a catalyst (for example tungstic acid), in particular ozone in combination with oxygen.

The invention relates both to the diacids and the α,ω-amino acids obtained according to the process of the invention.

According to one option, the process of the invention comprises an additional intermediate stage, between stage b) as defined above and stage c) as defined above, of nitrilation of the acid functional group of the monounsaturated fatty acid, resulting in an unsaturated nitrile.

According to yet another specific option, the process of the invention comprises a stage of nitrilation of the acid functional group of the saturated hydroxylated fatty acid resulting from stage a) with concomitant (or simultaneous) dehydration, resulting in an unsaturated nitrile.

Said nitrilation stage can be carried out in the liquid phase or in the gas phase using ammonia at a temperature generally of between 150° C. and 350° C. and with a catalyst.

More particularly, said nitrilation is carried out in the liquid phase with, as catalyst, a metal oxide which is zinc oxide. More particularly still, said nitrilation is carried out in the gas phase with said catalyst being, for example, supported on a fixed bed of doped or non-doped alumina.

According to the process of the invention, the effluent from the nitrilation stage can be subjected to the oxidative cleavage stage c) defined above, the effluent (comprising the nitrile-acid compound) of which is subjected to a hydrogenation d), as described below.

In particular, the hydrogenation stage is carried out at a temperature of between 70 and 200° C., preferably between 70 and 150° C. and more preferably between 90 and 130° C., under an $H_2$ pressure of between 1 and 300 bar, preferably between 5 and 50 bar, in the presence of either homogeneous or heterogeneous hydrogenation catalysts.

The hydrogenation of the unsaturated fatty acids is a well known reaction. Reference may be made, on this subject, to Vol. A 10 of Ullmann's Encyclopedia, pages 189, 207 to 209 and 267 to 269. This hydrogenation stage can be carried out at a temperature of between 70 and 150° C., preferably between 90 and 130° C. and more preferably at approximately 120° C., under an $H_2$ pressure of between 1 and 300 bar, preferably between 5 and 50 bar and more preferably at approximately 20 bar. The process is carried out in the presence of either homogeneous or heterogeneous hydrogenation catalysts and preferably heterogeneous hydrogenation catalysts. These catalysts will, for example, be noble metals, such as Pt, Pd or Rh, or transition metals, such as Mo, W, Cr, Fe, Co or Ni, used alone or as a mixture. They can be deposited on supports, such as active charcoal, alumina and silica. The preferred catalysts are Raney nickel or palladium-on-active charcoal. The amount of catalyst used represents from 0.2% to 5% by weight and preferably from 0.4% to 2% by weight of the treated feedstock.

The hydrogenation stage a) is preferably carried out under operational conditions such that the effluent resulting from this hydrogenation stage exhibits an iodine number <5, preferably <3 and more preferably <1 and a hydroxyl number >100 mg KOH/g.

The stage b) of dehydration of the saturated hydroxylated fatty acids is conventionally carried out at a temperature of between 200 and 300° C. in the presence of an acid catalyst. This catalyst can be sulfuric acid, phosphoric acid, sulfonic acids, alkyl sulfonates or ion-exchange acid resins, such as resins of Amberlyst® type or of other type.

A copious and long-standing literature exists on the dehydration of castor oil. Mention may in particular be made of the patents GB 671368, 687986, 691484, 703363 and U.S. Pat. No. 2,567,925, and also in the Kirk-Othmer Encyclopedia, Vol. 8, page 526. It should be noted that the dehydration results in a mixture of two monounsaturated fatty acids, the double bond which is located either in the "δ–n" position or in the "δ–n+1" position with respect to the acid functional group. On considering, for example, ricinoleic acid, the mixture will be δ11 plus δ12 and on considering, for example, lesquerolic acid, the mixture will be δ13 plus δ14.

The stage c) of oxidative cleavage of the double bond of the monounsaturated fatty acids or nitriles, which results in the formation of the acid functional group on the two carbons of the double bond, is also known per se. It can be carried out using a wide range of strong oxidizing agents.

The oxidative cleavage stage c) can be carried out by using, for example, a strong oxidizing agent, such as $KMnO_4$ in the concentrated form, and with heat, as is described in "Organic Chemistry" by L. G. Wade Jr., 5$^{th}$ Edition, Chapter 8: Reactions of Alkenes.

The oxidative cleavage can be obtained via a sulfuric acid/chromic acid derivative, such as described in the patent USP 2 871 247, in columns 2 and 3.

The oxidative cleavage stage c) can be carried out by using hydrogen peroxide, as described in the patent GB 743 491, optionally in combination with a catalyst. The use of $H_2O_2$ is also described in the patent WO 2007/039481 (Novamont).

Mention may also be made of the work "Angew. Chem. Int. Ed.", 2000, 39, pp. 2206-2224, which describes the oxidative cleavage of the double bond either with a peracid, in combination with a ruthenium-based catalyst, or with $H_2O_2$, with catalysts based on Mo, W or Re.

Numerous studies have been carried out on the use of ozone as oxidizing agent. Moreover, it is mentioned, in the "Angew. Chem." work cited above, that the oxidative cleavage of oleic acid to give pelargonic acid and azelaic acid is the most important industrial application of ozonolysis.

Oxidative ozonolysis is very widely used to carry out cleavage. The patent U.S. Pat. No. 2,813,113 describes in particular a process for the oxidative ozonolysis of a fatty acid, such as oleic acid, which consists, in a first stage, in treating the acid with oxygen in combination with ozone, in order to form ozonides, and then, in a second stage, in oxidizing the latter by the oxygen.

In this type of reaction, compounds which block the oxidation process at the stage of the ketones or aldehydes, in what is referred to as reductive ozonolysis, are not used.

Thus, the oxidative cleavage stage c) can be carried out by using ozone in combination with oxygen.

Another subject matter of the invention is diacids prepared according to the above process.

When the process of the invention is intended for the synthesis of ω-amino acid, it will comprise, on the one hand, an additional intermediate stage of nitrilation (ammoniation) of the acid functional group according to the reaction R—COOH+$NH_3$→R—CN+2 $H_2O$ and, on the other hand, a final stage of reduction of the nitrile functional group to give a primary amine functional group. The overall reaction scheme is described later.

Thus, in a specific embodiment of the invention, the process comprises an additional intermediate stage b'), between stage b) and stage c), of nitrilation of the acid functional group of the monounsaturated fatty acid resulting in an unsaturated nitrile.

Alternatively, the process can comprise a stage a'), between stage a) and stage b), of nitrilation of the acid functional group of the saturated hydroxylated fatty acid resulting from stage a), with concomitant dehydration, resulting (subsequent to dehydration) in an unsaturated nitrile.

The reaction for nitrilation (or ammoniation, the two terms being used without distinction) of the fatty acids is well known and follows the following simplified reaction scheme:

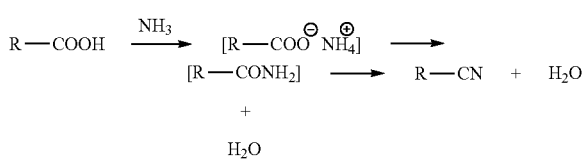

The nitrilation stage can be carried out in the liquid phase (batch process) or in the gas phase (continuous process) by means of ammonia, at a temperature generally of between 150° C. and 350° C., with a catalyst.

The liquid-phase process is carried out at a temperature of between 150° C. approximately (first phase) and 250°-300° C. (second phase) with a catalyst which is generally a metal oxide and most frequently zinc oxide.

In the continuous process, the reaction takes place in the gas phase at high temperature levels and generally over a catalyst consisting of a fixed bed of alumina, which is or is not doped. The fatty acid is vaporized in the presence of a large amount of ammonia, the excess of which is recycled. The process can thus be carried out in the gas phase with, as catalyst, a fixed bed of alumina, which is or is not doped.

In the gas-phase version, many other catalysts can be used and there exists copious literature on this subject. Mention may be made, for example, of the document JP 2000-16977, which describes catalysis with niobium oxide at a temperature of 260° C. (stearic acid), or the document JP 2000-7637, which describes a process carried out at a temperature ranging from 180° to 350° C., also with a catalyst of niobium oxide type. U.S. Pat. No. 6,005,134 describes catalysis with titanium and, finally, JP 10-195035 describes catalysis with iron-doped zirconium oxide.

In a specific embodiment of the invention, the effluent from the nitrilation stage is subjected to the oxidative cleavage stage c), the nitrile-acid effluent from which is subjected to a hydrogenation.

The final hydrogenation reaction of the nitrile-acid compound is carried out under conditions analogous to those described above for the initial hydrogenation reaction. Raney nickel, deposited or not deposited on a support, such as silica, is the catalyst most generally adopted. The use of other metals known for their catalytic activity in hydrogenation has also been envisaged under heterogeneous conditions. Mention may be made, for example, of platinum, palladium, ruthenium or iridium, alone or in combination. Mention may be made, on this subject, of GB 1 273 874, which describes the use of a ruthenium catalyst deposited on silica.

In one embodiment of the alternative form targeted at the synthesis of amino acids, it will be possible, in some cases, to carry out the ammoniation stage directly after the initial hydrogenation stage. This is because, under the conditions of the ammoniation, the dehydration of the hydroxylated fatty acid can occur spontaneously, which makes it possible to eliminate an intermediate stage.

In the case where the feedstock is composed of the crude oil, an additional hydrolysis stage is necessary and can occur either after the initial hydrogenation stage or after the hydrogenation and dehydration stages.

The operating conditions for the hydrolysis stage are well known to a person skilled in the art. They are described in particular in Ullmann's Encyclopedia, Vol. A 10, pages 188 and 254 to 260.

Naturally, it is perfectly possible to carry out, between each stage, the separation of the compounds reacting in the following stage from the "useless" compounds.

Likewise, at the end of the process, it is necessary to separate the two forms of amino acids or of diacids, for example the $C_{11}$ and $C_{12}$ forms or the $C_{13}$ and $C_{14}$ forms originating from the dehydration stage.

The techniques of the separation of fatty acids in a mixture are well known and are extensively described in Ullmann's Encyclopedia, Vol. A 10, pages 260 to 267. They are essentially based on distillation and crystallization and their various alternative forms. The choice of the technique will depend on the difference in the temperatures of change of state of the constituents of the mixture, liquid/gas (distillation) or liquid-solid (crystallization). It is also possible to envisage liquid-liquid extractions using suitable solvents or chromatographic separations.

In an alternative embodiment of the process of the invention, it is possible to envisage enriching the reaction medium in one of the targeted amino acids or diacids by adding thereto, during processing, either after the initial dehydrogenation stage or after the dehydration stage, a fatty acid comprising just one olefinic unsaturation in a suitable position δ11, δ12, δ13 or δ14. By way of examples, it will be possible to add, to the medium, if the main target is the $C_{11}$ amino acid, vaccenic acid and/or gondoic acid. Likewise, it will be possible to add, to the medium, erucic acid in order to increase the proportion of $C_{13}$ diacid or $C_{13}$ nitrile-acid.

The process is particularly advantageous for feedstocks comprising densipolic acid and auricolic acid, as or not as a mixture with ricinoleic acid and lesquerolic acid, as, after hydrogenation, saturated acids having the same $C_{18}$ or $C_{20}$ chain length are obtained.

In the implementation of the process of the invention, the choice will preferably be made of feedstocks rich in ricinoleic acid or densipolic acid, resulting in $C_{11}$ or $C_{12}$ nitrile-acids resulting in the corresponding ω-amino acids, and feedstocks rich in lesquerolic acid or auricolic acid, resulting in the $C_{13}$ or $C_{14}$ diacids.

The process of the invention makes it possible to synthesize, depending on the alternative form employed, either a fatty diacid or a fatty amino acid comprising from 11 to 14 carbon atoms per molecule, this depending on the composition of the feedstock treated.

The reaction schemes of the process are illustrated below taking as example ricinoleic acid, which is the commonest of the unsaturated hydroxylated fatty acids. If the feedstock treated is in the ester form, the reaction schemes below will be identical except that the H of the acid functional group is replaced by an alkyl radical (simple alcohol ester, such as methyl ester, for example) or by a radical comprising 2 or 3 carbon atoms respectively carrying 1 or 2 alcohol or ester functional groups (polyol esters, such as glycerol esters, for example).

Diacid Alternative Form

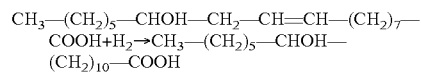

The dehydration results in a mixture of unsaturated fatty acids according to

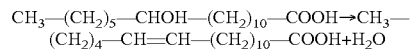

or

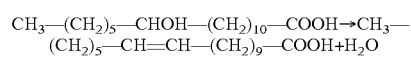

Oxidative cleavage thus results in a mixture of diacids

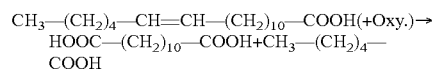

and

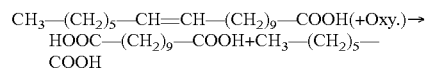

Amino Acid Alternative Form

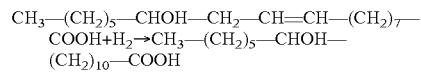

The dehydration results in a mixture of unsaturated fatty acids according to

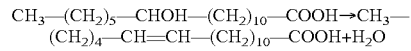

or

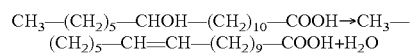

The nitrilation results in the fatty nitriles according to

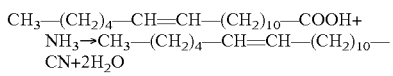

or

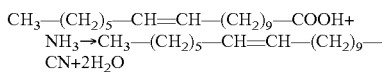

Oxidative cleavage thus results in a mixture of nitrile-acids

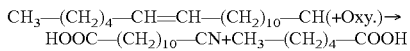

and

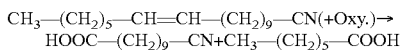

Finally, the hydrogenation of the nitrile-acids results in the amino acids according to

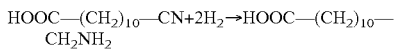

and

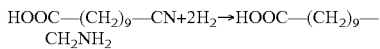

The stage of nitrilation of the fatty acids occurs after the hydrogenation stage. It can follow the dehydration stage but, in some cases, the nitrilation conditions will make possible the concomitant dehydration of the saturated hydroxylated fatty acid, which will be particularly advantageous.

Another subject matter of the invention is ω-amino acids prepared according to the above process.

At a practical level, the process will preferably be able to comprise the sequence of following stages, starting from a feedstock of natural origin comprising unsaturated hydroxylated fatty acids in the ester form (alcohol or polyol ester, such as glycerol ester) and in particular in the form of hydroxylated oil of corresponding fatty acid (the oil being a glycerol ester), with said stages being:
i) hydrogenation of the hydroxylated ester, in particular the corresponding oil
ii) dehydration of the hydrogenated hydroxylated ester, in particular of the corresponding oil
iii) hydrolysis of the hydrogenated (and dehydrated) ester, in particular of the corresponding oil, in order to obtain the corresponding unsaturated fatty acid and alcohol or polyol, in particular glycerol
iv) separation of the alcohol or polyol, in particular glycerol, and optionally separation of the unsaturated fatty acid isomers (for example, separation of the 11-octadecanoic from the 12-octadecanoic)
v) optionally (only in the case of nitrile), ammoniation of the unsaturated (fatty) acid in order to obtain the corresponding unsaturated nitrile
vi) oxidative cleavage of the unsaturated nitrile or fatty acid (as the case may be)
vii) optionally, separation of the cleavage products and light acids formed (for example, of the 11-nitrile-acid from the 12-nitrile-acid, in the case of the nitrile)
viii) optionally (case of nitrile), hydrogenation of the nitrile-acid in order to form the corresponding amino acid
ix) separation and purification of the diacid formed or of the amino acid formed, as the case may be.

According to another more specific option of said process where the objective is first a nitrile-acid and then a corresponding amino acid, said ω-functionalized acid is thus an amino acid and said feedstock of natural origin comprises unsaturated hydroxylated fatty acids in the ester (alcohol or polyol ester, such as glycerol ester) form, in particular in the form of a hydroxylated oil (glycerol ester), and said process comprises the sequence of the following stages:
i) hydrogenation of the hydroxylated ester, in particular of the corresponding oil
ii) hydrolysis of the hydrogenated ester, in particular of the corresponding oil, in order to obtain the corresponding saturated fatty acid (for example 12-hydroxystearic acid) and alcohol or polyol, in particular glycerol
iii) separation of the alcohol or polyol, in particular glycerol, with optional separation of the saturated fatty acids from the hydroxylated fatty acids
iv) ammoniation of the saturated hydroxylated acid, with simultaneous dehydration, in order to obtain the corresponding unsaturated nitrile
v) optionally, separation of the unsaturated nitrile isomers
vi) oxidative cleavage of the unsaturated nitrile
vii) optionally, separation of the nitrile-acid cleavage products and of the light acids formed
viii) hydrogenation of the nitrile-acid, in order to obtain the corresponding amino acid
ix) separation and purification of the amino acid obtained.

In the case where the objective is a nitrile-acid and then an amino acid, starting from a vegetable oil source which has a low concentration of hydroxylated acid, it is possible to provide a slightly different sequence:
i) alcoholysis (for example or in particular methanolysis) of the vegetable oil, optionally concomitant with its extraction from the seed
ii) extraction of a fraction rich in hydroxylated acid ester
iii) hydrogenation of the hydroxylated ester
iv) optionally, hydrolysis of the hydrogenated ester in order to obtain the corresponding fatty acid (for example, production of 12-hydroxystearic acid or 14-hydroxyeicosanoic acid)
v) ammoniation of the saturated hydroxylated acid with simultaneous dehydration (including on ester of stage iii) or on acid of stage iv)), in order to obtain the unsaturated nitrile
vi) optionally, separation of the unsaturated nitrile isomers
vii) oxidative cleavage of the unsaturated nitrile
viii) optionally, separation of the nitrile-acid cleavage products (comprising 11 and 12 carbons, for example) and of the light acids formed
ix) hydrogenation of the nitrile-acid
x) separation and purification of the amino acid.

The examples which follow illustrate in an even more detailed manner the present invention, without any limitation, by these examples, of its coverage.

EXPERIMENTAL PART

Example 1

Production of *Lesquerella* Oil

The procedure with regard to 25 kg of seeds is as follows:
1. Flaking of the fresh *lesquerella* seed on a smooth roll crusher.
2. The flakes are subsequently dried at 100° C. for 16 h.
3. The flakes are introduced into a percolation column.
4. The methanol/hexane (50/50 by weight) mixture is then circulated over the bed at 40° C. for 30 minutes.

5. The miscella is subsequently withdrawn and the bed of flakes is subsequently washed by 5 successive washing operations with the methanol/hexane mixture at 40° C. (5 minutes per washing operation).
6. The miscella is then evaporated under vacuum at 90° C. under 20 mbar for 5 min.
7. The oil and the gums are separated by centrifuging. The oil yield is calculated on the basis of the weight of oil obtained versus the theoretical weight of oil expected.
8. The oil is subsequently washed to neutrality by addition of hot water and centrifuging and then it is dried under vacuum at 90° C. and 20 mbar for 5 min. The acid number and the composition of this oil are then measured.

TABLE A

Mass balance of the process of nonreactive trituration of the *lesquerella* seed in the presence of a methanol/hexane mixture

| Conditions | Test 10-E47 |
|---|---|
| Close-spaced smooth roll crusher | Yes |
| Drying 100° C., 16 h | Yes |
| Flake thickness, mm | 0.16 to 0.18 |
| Solvents/Seed ratio by weight | 2 |
| Test Balance | |
| Solids yield (Yd), % (1) | 107.8 |
| Phase separation | No |
| Oil Yd, % | 107.8 |
| Oil potential in the oil cake, % | 2.4 |
| (Oil cake MG content, %) | (0.9) |
| Yd of insoluble materials in the oil extracted by centrifuging, % | 0.0 |
| Oil loss (calculated value), % (2) | −10.2 |

(1) The solids yield is the ratio, times 100, of the solids obtained after evaporation of the miscella to the sum of the theoretical amounts of theoretical oil
(2) Oil loss = 100 − Oil Yd − Oil cake oil pot.

Comments:

In the presence of a methanol/hexane mixture, the extraction yield is of the same order as with methanol alone (≈108%), whereas the extraction temperature was reduced to 40° C. in order to prevent the hexane from boiling;

the content of insoluble material is zero, appearing to indicate that, if there had been extraction of gums, the latter are partially liposoluble (<10% in the oil);

the oil cake remains relatively well extracted (0.9%);

the phospholipids content of the oil is 1.3%;

qualitatively, the extracted oil is highly acidic (AN>11). It is highly probable that the dissolved gums exhibit a significant acidity. Furthermore, the expected content of lesquerolic acid (52%) is found.

TABLE 1

Analysis of the oil extracted with a methanol/hexane mixture

| Criteria | Method | Test 10-E47 oil |
|---|---|---|
| Acid number (mg KOH/g) | EN 14104 | 11.2 |
| Fatty acids profile | EN14105 | |
| Palmitic (C16:0) | | 1.6 |
| Palmitoleic (C16:1) | | 0.9 |
| Stearic (C18:0) | | 2.3 |
| Oleic (C18:1) | | 18.8 |
| Ricinoleic (C18:1-OH) | | 0.5 |
| Linoleic (C18:2) | | 10.1 |
| Densipolic (18:2-OH) | | 0.2 |
| Linolenic and arachidic | | 11.6 (1) |
| Eicosenoic (C20:1) | | 0.9 |
| Lesquerolic (C20:1-OH) | | 52.1 |
| Auricolic (20:2-OH) | | 2.6 |

TABLE 1-continued

Analysis of the oil extracted with a methanol/hexane mixture

| Criteria | Method | Test 10-E47 oil |
|---|---|---|
| Phospholipids (%) | Internal | 1.3 (2) |
| Corrected yield of oil (3), % | — | 106.5 |

(1) The two peaks are coeluted. Linolenic acid is predominant
(2) Calculated value; % phospholipids = % phosphorus × 26
(3) Corrected Yd = Extraction Oil Yd (Table 1) − % phospholipids The oil thus obtained is subsequently refined by neutralization with sodium hydroxide and degumming with diluted phosphoric acid, so as to remove the phospholipids. Finally, the oil is dried under vacuum. The oil obtained has the following characteristics:

Acid number: 0.5 mg KOH/g
Saponification number: 175 mg KOH/g
Hydroxyl number: 100 mg KOH/g
Iodine number: 95 g $I_2$/100 g
Lesquerolic acid content: 52%
Phosphorus content: 10 ppm
Water and volatiles content: 0.1% by weight
Ash content: 0.1% by weight.

Example 2

Preparation of Hydrogenated *Lesquerella* Fatty Acids

In a first step, the *lesquerella* oil is transesterified, then hydrogenated and, finally, hydrolyzed. An extraction stage after the transesterification makes it possible to enrich the product in lesquerolic acid ester.

The methanolysis of the *lesquerella* oil is carried out with a methanol/oil molar ratio of 6 (i.e., twice the stoichiometric amount). The catalyst used is sodium methoxide at a content of 0.5% by weight and the reaction temperature is 60° C. The constituents are mixed with vigorous stirring for 30 minutes. After methanolysis (transesterification) and removal of the glycerol by separation by settling, the esters are purified by washing with water and drying under vacuum. The specifications of the methyl esters are as follows:

Acid number: 0.5 mg KOH/g
Saponification number: 175 mg KOH/g
Iodine number: 95 g $I_2$/100 g
Content of residual glycerides (analysis by GPC): 1.9% by weight
Lesquerolic acid content: 52%

The mixed methyl esters obtained in the preceding stage are hydrogenated in an autoclave (in several goes, as a result of the size of the autoclave). Use is made of a catalyst of Raney nickel type supplied by Johnson Matthey, at a content of 0.5% by weight. The hydrogenation temperature is 150° C., under a hydrogen pressure of 8 bar. This stage results in a product having an iodine number of 3 g $I_2$/100 g and a hydroxyl number of 93 mg KOH/g.

Finally, a saponification stage is carried out by addition of sodium hydroxide to the mixture of esters and then an acidification stage is carried out with sulfuric acid. The resulting mixture is washed with water, separated by settling and dried under vacuum. The fatty acid mixture obtained has the following characteristics:

Acid number of 180 mg KOH/g
Hydroxyl number of 90 mg KOH/g
Iodine number of 3 g $I_2$/100 g The 14-hydroxyeicosanoic acid content is 50%.

Example 3

Preparation of a Mixture Enriched in 14-Hydroxyeicosanoic Acid

The mixture of esters resulting from the transesterification stage as in example 2, but starting from a commercial *lesquerella* oil, is subjected to a stage of liquid-liquid extraction with a methanol/hexane mixture. In a practical implementation of the example, the methanol comprises 5% by weight of water. The nonhydroxylated fatty acids are more compatible with the hexane phase, whereas the hydroxylated fatty acids, such as lesquerolic acid, are more compatible with the methanolic phase.

In this example, the hexane was used as nonpolar solvent. As a reminder, the polar solvent consists of hydrated methanol. A succession of depleting and enriching stages is carried out.

1. 5 g (methyl ester of *lesquerella* oil)+30 ml of nonpolar solvent+15 ml of polar solvent are stirred for 5 minutes in a separating funnel and give a heavy phase HP1+light phase LP1.
2. The light phase LP1 is taken up with 15 ml of polar solvent and again gives a heavy phase HP2 and a light phase LP2.
3. The heavy phase HP1 and the heavy phase HP2 are taken up with 30 ml of nonpolar solvent and again give a heavy phase HP3 and a light phase LP3.
4. The heavy phase HP3 is taken up with 30 ml of nonpolar solvent to give a heavy phase HP4 and a light phase LP4.

The fractions recovered are subsequently concentrated by evaporation of the solvents.

1. The heavy phase HP4 gives the polar fraction.
2. The light phases LP2+LP3+LP4 are combined to give the nonpolar fraction.

TABLE 2

Analytical balance of the esters resulting from the extraction

| | Starting material | Heavy phase | Light phase |
|---|---|---|---|
| Polar solvent | | 95% Methanol | 95% Methanol |
| Nonpolar solvent | | Hexane | Hexane |
| Yd by weight, % | | 16.5 | 83.5 |
| Methyl lesquerolate extraction, Yd, % | | 25.4 | 74.8 |
| Acid number | 0.72 | nd | 1.12 |
| Me C16:1 (%) | 0.5 | 0.1 | 0.6 |
| Me C16 (%) | 1.3 | 0.1 | 1.6 |
| Me C18:2 (%) | 9.1 | 0.6 | 11.7 |
| Me C18:1 (%) | 23.5 | 0.3 | 27.5 |
| Me C18:0 (%) | 1.8 | 0.1 | 2.2 |
| Me C20:0 (%) | 0.9 | 0.0 | 1.1 |
| Me C20:1 (%) | 1.0 | 0.0 | 0.7 |
| Me C18:1-OH (%) | 0.3 | 0.2 | 0.3 |
| Me C20:1-OH (%) | 60.3 | 92.9 | 54.0 |
| MonoGlyceride (%) | 1.7 | 5.8 | 0.8 |
| DiGlyceride (%) | 0.1 | 0.0 | 0.1 |
| TriGlyceride (%) | 0.0 | 0.0 | 0.0 |

With regard to the fraction enriched in lesquerolic acid, a hydrogenation and a hydrolysis are carried out, as in the preceding example, in order to obtain a mixture rich in 14-hydroxyeicosanoic acid.

The characteristics of the mixture obtained are:
Acid number of 1 mg KOH/g
Hydroxyl number of 145 mg KOH/g
Iodine number of 3 g $I_2$/100 g
14-Hydroxyeicosanoic acid content of 89%.

Example 4

Preparation of 12-Hydroxystearic Acid

In this example, the procedure is carried out as in example 6.1, test 09-E08, of the patent application WO 2010/076527, by reactive trituration of castor oil plant seeds. The mixture of methyl esters is subsequently hydrogenated and hydrolyzed. As in example 2, a mixture rich in 12-hydroxystearic acid is obtained.

After the reactive trituration stage, a mixture of methyl esters having an acid number of 0.46 mg KOH/g is obtained, comprising 0.85% of palmitic acid ester, 2.9% of linoleic acid ester, 3.46% of oleic acid ester, 0.96% of stearic acid ester and 90.65% of ricinoleic acid ester. The mixture also comprises 1.19% of monoglycerides.

The mixture of esters is then hydrogenated in the presence of a Raney nickel catalyst (1% by weight), under a pressure of 20 bar of hydrogen and at a temperature of 130° C. The reaction is carried out in 2 hours. The final product is subsequently saponified with sodium hydroxide and acidified with sulfuric acid. After washing, a mixture rich in 12-hydroxystearic acid is obtained, comprising 0.9% of palmitic acid, 0.3% of linoleic acid, 0.4% of oleic acid, 7.8% of stearic acid and 90% of 12-hydroxystearic acid.

Example 5

Preparation of Isooleonitrile (this Expression is Used to Indicate a Mixture of Unsaturated Isomers Comprising 18 Carbon Atoms) from Commercial 12-hydroxystearic Acid In this example, use is made of a commercial 12-hydroxystearic acid supplied by Mosselman. This batch has the following specifications:
Acid number: 177 mg KOH/g
Saponification number: 182.5 mg KOH/g
Iodine number: 2.3 g $I_2$/100 g
Hydroxyl number: 162.7 mg KOH/g.

This stage consists in reacting ammonia with the fatty acid at high temperature in the presence of a catalyst (zinc oxide), in order to obtain the corresponding nitrile. The reaction mechanism is probably a conversion of the acid to the ammonium salt, then to the amide and finally to the nitrile. Due to the extreme conditions of this reaction, the hydroxylated acid simultaneously dehydrates.

In order to carry out this reaction, use is made of an arrangement consisting of a reactor heated by a heating mantle, surmounted by a condenser (dephlegmator) which returns the heavy compounds to the reactor and allows the water resulting from the reaction and also the excess ammonia to pass. The reactor is fed with gaseous ammonia. The ammonia bottle is positioned on a balance in order to be able to monitor the amount used.

250 g of 12-hydroxystearic acid are charged to the reactor. 0.16 g of zinc oxide catalyst is added. The temperature of the mixture is brought up to the melting of the acid (82° C.) and then, with stirring to 205° C. At this temperature, the ammonia is added to the reactor, the flow rate being gradually increased up to 0.417 liters/minute·kg. Subsequently, the temperature of the reactor is increased up to 300° C. The temperature of the dephlegmator is maintained at 130° C.

The temperature of the reactor is maintained at 300° C. until an acid number of less than 0.1 mg KOH/g is achieved. The progress of the reaction is followed by measuring the acid number and the amount of water condensed at the reactor outlet. In the present case, the excess ammonia is not recycled but it can be recycled industrially. After reacting for 10 hours and after the addition of 72 g of ammonia, the reaction is halted. 189.5 g of product are recovered (but a portion of the losses is related to the numerous samplings during the synthesis). The crude product is subsequently distilled under a pressure reduced to 16 mbar with a Vigreux column, which amounts to removing the heavy products. The distillation is carried out at a temperature of 216 to 289° C. in the boiler and 205 to 219° C. at the distillation column top. The whole of the product has passed in 20 minutes. 159 g of distillate and 15.3 g of top fraction are recovered for 13 g of distillation concentrate (heavy fraction), i.e. a distillation yield of 92%.

The product resulting from this reaction is analyzed by gas chromatography, on an HP5890 series II chromatograph, with an HP5 column (30 m).

The crude product obtained comprises 0.9% by weight of palmitonitrile, 86.3% by weight of isooleonitrile, 9.1% by weight of stearonitrile, 0.4% by weight of linoleonitrile, 0.3% by weight of eicosenonitrile and 0.3% by weight of eicosanonitrile.

Example 6

Preparation of the Nitrile from the 12-hydroxystearic Acid Obtained According to Example 4

The procedure is carried out as in the preceding example but starting from the 12-hydroxystearic acid obtained according to example 4. A mixture rich in isooleonitrile is obtained, comprising 0.9% of palmitonitrile, 0.2% of linoleonitrile, 8.0% of stearic acid and 90.4% of isooleonitrile.

Example 7

Preparation of Isooleic Acid, Obtained by Dehydration of 12-hydroxystearic Acid, and Preparation of the Corresponding Nitrile Use is made, for this example, of the commercial 12-hydroxystearic acid of example 5. The dehydration reaction is followed by monitoring the iodine number and the hydroxyl number. In order to carry out this reaction, an Amberlyst® 15 acid resin is used as catalyst at a concentration of 5% by weight. At a reaction temperature of 120° C. and under a high vacuum of 400 mbar, in order to remove the water produced by the reaction, a product having an iodine number of 68 and a hydroxyl number of 6 was obtained.

Under the same conditions and at a temperature of 150° C., a zero hydroxyl number is obtained, with an iodine number of 75.

The crude product obtained comprises 1.0% by weight of palmitic acid, 85.2% by weight of isooleic acid, 9.2% by weight of stearic acid, 0.3% by weight of linoleic acid, 0.3% by weight of eicosenoic acid and 0.3% by weight of eicosanoic acid.

Example 7a

Preparation of Isooleic Acid by Dehydration of 12-hydroxystearic Acid and Preparation of the Corresponding Nitrile Use is made, for this example, of the commercial 12-hydroxystearic acid of example 5. The dehydration reaction is followed by monitoring the iodine number and the hydroxyl number. In order to carry out this reaction, a silica/alumina catalyst comprising 10% of alumina (having a specific surface of 406 m$^2$/g) is used as catalyst at a concentration of 10% by weight. At a reaction temperature of 180° C., under a partial vacuum in order to remove the water produced by the reaction, a product having an iodine number of 72 and a hydroxyl number of 6 is obtained.

Example 7b

Preparation of Isooleic Acid by Dehydration of 12-hydroxystearic Acid

Use is made, for this example, of the mixture of hydrogenated methyl esters produced according to example 4. The dehydration reaction is followed by monitoring the iodine number and the hydroxyl number. In order to carry out this reaction, use is made of sulfuric acid (0.1%) and an activated clay (1.0% by weight) as catalyst. The reaction takes place at a temperature of 180° C. for a duration of 3 hours and under a partial vacuum, in order to remove the water produced by the reaction. After reaction, the product is washed and dried in order to remove the catalyst. A product having an iodine number of 55 and a hydroxyl number of 2 is obtained.

Example 8

Preparation of Isoeicosenonitrile from the 14-hydroxyeicosanoic Acid Resulting from Example 2

The procedure is carried out as in example 5, starting from the 14-hydroxyeicosanoic acid resulting from example 2, and a mixture of nitriles comprising 51% of isoeicosenonitrile is obtained. The increase in the content of C20:1 nitrile with respect to the lesquerolic acid can be explained by the high reactivity of the polyunsaturated acids during the conversion to nitriles, these resulting in heavy products which are removed in the distillation concentrate.

Example 9

Preparation of Isoeicosenonitrile from the 14-hydroxyeicosanoic Acid Resulting from Example 3

The procedure is carried out as in the preceding example 8 with the mixture rich in 14-hydroxyeicosanoic acid of example 3. A mixture of nitriles comprising 90% of isoeicosenonitrile is obtained.

Example 10

Oxidative Cleavage with Hydrogen Peroxide of the Isooleonitrile Resulting from Example 5

25 g of product obtained, such as in example 5, are mixed with 250 mg of tungstic acid in a jacketed reactor. With mechanical stirring, the temperature is regulated at 70° C. and approximately 7 grams of 70% by weight hydrogen peroxide ($H_2O_2$) are added dropwise over approximately 7 minutes. After a reaction time of 2 hours, the aqueous phase is removed by separation by settling. 250 mg of tungstic acid are again added to the organic phase and 7 g of 70% hydrogen peroxide are again added dropwise as above. This operation is repeated after a reaction time of 4 h, 22 h, 24 h and 26 h, with a total duration of the test of 28 hours and 42 g of $H_2O_2$ added.

After separation of the final fraction of aqueous phase, the organic phase is washed with water, then dried under vacuum and analyzed by chromatography.

The composition of the mixture obtained indicates a yield of hexanoic acid of 10.4 mol %, of heptanoic acid of 12.3% by weight, of 10-cyanodecanoic acid of 13.1% by weight and of 11-cyanoundecanoic acid of 12.1% by weight.

This distribution confirms that the reaction for the dehydration of 12-hydroxystearic acid which took place during the formation of the nitrile results in the two unsaturated isomers C18:1 δ-11 and C18:1 δ-12.

Example 11

Oxidative Cleavage with Hydrogen Peroxide of the Isooleic Acid Obtained in Example 7

The procedure is carried out as in example 10 but with the acid mixture rich in isooleic acid resulting from example 7.

The yield is 8% of heptanoic acid and 7.1% of hexanoic acid. These two acids are the easiest to analyze and characterize oxidative cleavage of the medium. After esterification of the mixture obtained, the quantification of the diacids produced indicates a yield of diacids of 8.5% of undecanedioic acid and of 7.5% of dodecanedioic acid.

Example 12

Ozonolysis of the Isoeicosenonitrile Obtained in Example 8 and Hydrogenation of the Nitrile Acid (Cyanoacid) Obtained to Give the Corresponding Amino Acid This example illustrates the oxidative cleavage of the unsaturated nitrile resulting from example 8 by ozonolysis to form the nitrile-acids of formulae $CN-(CH_2)_{11}-COOH$ and $CN-(CH_2)_{12}-COOH$.

Ozone obtained by a Ozania ozone generator is bubbled into 50 grams of a nitrile obtained in accordance with example 8. An amount of ozone of 50 g/h, at a concentration of 6% in pure oxygen, is produced. The entire apparatus is made of glass. During this stage, with a duration of 4 hours, the temperature of solution is kept below 30° C. In order to carry out the conversion of the ozonide to the nitrile-acid, the temperature is first of all raised to approximately 60° C. When the reaction for decomposition of the ozonide begins, it is accompanied by a raise in the temperature. A stream of oxygen is continuously added in order to maintain the temperature and in order to directly oxidize the products resulting from the decomposition of the ozonide. The procedure is carried out over 4 hours in order to limit the formation of decomposition products. It is important to maintain the reaction temperature slightly above the temperature of the decomposition of the ozonide during this stage. A temperature of 95° C. is used in this example.

A yield of 91 mol % of a mixture of 10-cyanodecanoic acid and 11-cyanoundecanoic acid is obtained.

15 g of nitrile-acid are dissolved in 160 g of ethanol. The solution is placed in a stirred autoclave with 3 g of Raney nickel catalyst; 15 g of ammonia and a pressure of 110 bar of hydrogen are then added. The temperature is raised to 100° C. and the pressure increases up to 139 bar. The conditions are maintained for 4 hours. The autoclave is cooled and the contents are filtered in order to recover the catalyst. 50 g of water are then added and the alcohol is distilled off. The resulting solution is titrated with dilute hydrochloric acid and the mixture of amino acids is filtered off, washed and treated under reflux of acetone and dried.

Example 13

Ozonolysis of the Isoeicosenonitrile Obtained in Example 9

The procedure is carried out as in example 12. On conclusion of the ozonolysis stage, the reaction mixture consists predominantly of heptanoic acid and hexanoic add, and also of cyanoacids. The heptanoic acid and hexanoic acid are removed by washing with hot water. The cyanoacids are recovered by extraction with cyclohexane at low temperature and recrystallization. The mixture of cyanoacids is then hydrogenated as in example 12.

The invention claimed is:

1. A process for the synthesis of ω-functionalized acids, wherein said acids are of formula $R-(CH_2)_n-COOH$, in which R represents COOH or $NH_2CH_2$ and n represents an integer between 9 and 12, they are obtained from a feedstock of natural origin comprising unsaturated hydroxylated fatty acids in the acid, ester or polyol ester form comprising at least 18 carbon atoms per molecule and in that said process comprises the following stages:
   a) hydrogenation of the unsaturated hydroxylated fatty acids, resulting in saturated hydroxylated fatty acids,
   b) dehydration of the saturated hydroxylated fatty acids, resulting in monounsaturated fatty acids,
   c) oxidative cleavage at the double bond of the monounsaturated fatty acids, resulting in an α,ω-bifunctional compound from diacid or nitrile-acid.

2. The process as claimed in claim 1, wherein the hydrogenation stage a) is carried out at a temperature of between 70 and 180° C. under an $H_2$ pressure of between 1 and 300 bar in the presence of either homogeneous or heterogeneous hydrogenation catalysts.

3. The process as claimed in claim 2, wherein said catalysts are noble metals, such as Pt, Pd or Rh, or transition metals, such as Mo, W, Cr, Fe, Co or Ni, used alone or as a mixture, optionally in the form supported on active charcoal, on alumina and on silica.

4. The process as claimed in claim 2, wherein said catalysts are chosen from Raney nickel and/or palladium-on-active charcoal.

5. The process as claimed in claim 1, wherein the hydrogenation stage a) is carried out under operational conditions such that the effluent resulting from this hydrogenation stage exhibits an iodine number <5 and a hydroxyl number >100 mg KOH/g.

6. The process as claimed in claim 1, wherein the stage b) of dehydration of the saturated hydroxylated fatty acids is carried out at a temperature of between 100 and 300° C. and in the presence of an acid catalyst.

7. The process as claimed in claim 1, wherein the oxidative cleavage stage c) is carried out using an oxidizing agent selected from the group consisting of $KMnO_4$, hydrogen peroxide, and oxidizing ozone, optionally in combination with a catalyst.

8. The process as claimed in claim 1, wherein it comprises an additional intermediate stage, between stage b) and stage c), of nitrilation of the acid functional group of the monounsaturated fatty acid, resulting in an unsaturated nitrile.

9. The process as claimed in claim 1, wherein it comprises a stage of nitrilation of the acid functional group of the saturated hydroxylated fatty acid resulting from stage a) with concomitant dehydration, resulting in an unsaturated nitrile.

10. The process as claimed in claim 8, wherein the nitrilation stage is carried out in the liquid phase or in the gas phase using ammonia at a temperature generally between 150° C. and 350° C. and with a catalyst.

11. The process as claimed in claim 10, wherein said nitrilation is carried out in the liquid phase with, as catalyst, a metal oxide which is zinc oxide.

12. The process as claimed in claim 10, wherein said nitrilation is carried out in the gas phase with said catalyst being supported on a fixed bed of doped or non-doped alumina.

13. The process as claimed in claim 8, wherein the effluent from the nitrilation stage is subjected to the oxidative cleavage stage c), the effluent (comprising the nitrile-acid compound) of which is subjected to a hydrogenation d).

14. The process as claimed in claim 13, wherein said hydrogenation is carried out at a temperature of between 70 and 200° C. under an $H_2$ pressure of between 1 and 300 bar in the presence of either homogeneous or heterogeneous hydrogenation catalysts.

15. The process as claimed in claim 1, wherein said ω-functionalized acid is a diacid or an amino acid and in that said feedstock of natural origin comprises unsaturated hydroxylated fatty acids in the ester form (alcohol or polyol ester, such as glycerol ester) with said stages being:
   i) hydrogenation of the hydroxylated ester,
   ii) dehydration of the hydrogenated hydroxylated ester,
   iii) hydrolysis of the hydrogenated (and dehydrated) ester in order to obtain the corresponding unsaturated fatty acid and alcohol or polyol,
   iv) separation of the alcohol or polyol and optionally separation of the unsaturated fatty acid isomers,
   v) optionally (only in the case of nitrile), ammoniation of the unsaturated (fatty) acid in order to obtain the corresponding unsaturated nitrile,
   vi) oxidative cleavage of the unsaturated nitrile or fatty acid (as the case may be),
   vii) optionally, separation of the cleavage products and light acids formed,
   viii) optionally (case of nitrile), hydrogenation of the nitrile-acid in order to form the corresponding amino acid, and
   ix) separation and purification of the diacid formed or of the amino acid formed, as the case may be.

16. The process as claimed in claim 1, wherein said ω-functionalized acid is an amino acid and in that said feedstock of natural origin comprises unsaturated hydroxylated fatty acids in the ester form and said process comprises the sequence of the following stages:
   i) hydrogenation of the hydroxylated ester,
   ii) hydrolysis of the hydrogenated ester in order to obtain the corresponding saturated fatty acid and alcohol or polyol,
   iii) separation of the alcohol or polyol with optional separation of the saturated fatty acids from the hydroxylated fatty acids,
   iv) ammoniation of the saturated hydroxylated acid, with simultaneous dehydration, in order to obtain the corresponding unsaturated nitrile,
   v) optionally, separation of the unsaturated nitrile isomers,
   vi) oxidative cleavage of the unsaturated nitrile,
   vii) optionally, separation of the nitrile-acid cleavage products and of the light acids formed,
   viii) hydrogenation of the nitrile-acid, in order to obtain the corresponding amino acid, and
   ix) separation and purification of the amino acid obtained.

17. The process as claimed in claim 1, wherein said ω-functionalized acid is an amino acid via a nitrile-acid, starting from a vegetable oil source which has a low concentration of hydroxylated acid, with a sequence of following stages:
   i) alcoholysis of the vegetable oil, optionally concomitant with its extraction from the seed,
   ii) extraction of a fraction rich in hydroxylated acid ester,
   iii) hydrogenation of the hydroxylated ester,
   iv) optionally, hydrolysis of the hydrogenated ester in order to obtain the corresponding fatty acid,
   v) ammoniation of the saturated hydroxylated acid with simultaneous dehydration (including on ester of stage iii) or on acid of stage iv)), in order to obtain the unsaturated nitrile,
   vi) optionally, separation of the unsaturated nitrile isomers,
   vii) oxidative cleavage of the unsaturated nitrile,
   viii) optionally, separation of the nitrile-acid cleavage products and of the light acids formed,
   ix) hydrogenation of the nitrile-acid in order to obtain the amino acid, and
   x) separation and purification of the amino acid obtained.

18. A process for the synthesis of an unsaturated fatty nitrile from a charge of natural origin containing unsaturated hydroxylated fatty acids in the acid ester or polyol ester form and bearing at least 18 carbon atoms per molecule, wherein said process comprises the following steps:
   a) hydrogenation of the unsaturated hydroxylated fatty acids leading to saturated hydroxylated fatty acids,
   b) dehydration of the saturated hydroxylated fatty acids leading to monounsaturated fatty acids, and
   c) nitrilation after step b) of the acid function of said mono unsaturated acid, thus leading to an unsaturated fatty nitrile.

19. The process in claim 18, which further comprises a nitrilation step of the acid function of said saturated hydroxylated fatty acid issued from step a), with simultaneous dehydration step b) of said acid and this leading to said unsaturated fatty nitrile.

20. The process of claim 18, wherein the said nitrilation step occurs in liquid phase or in gas phase using ammonia at a temperature between 150° C. and 350° C., with a catalyst.

21. The process of claim 20, wherein the said nitrilation occurs in liquid phase with a catalyst as a metallic oxide which is zinc oxide.

22. The process of claim 20, wherein the nitrilation step occurs in gas phase with said catalyst being supported by an alumina fixed bed, which may be doped or not doped.

23. A process of synthesis of an unsaturated fatty nitrile from a natural origin charge, comprising unsaturated hydroxylated fatty acids in the form of an ester which is an oil of hydroxylated fatty acid, the process comprising the steps of:
   i) hydrogenation of said oil,
   ii) dehydration of the hydrogenated hydroxylated oil of step i),
   iii) hydrolysis of the hydrogenated and dehydrated oil of step ii) for obtaining the corresponding unsaturated acid and glycerol,
   iv) separation of the glycerol, and
   v) ammoniation of the unsaturated fatty acid for obtaining the corresponding unsaturated fatty nitrile.

24. The process of claim 23, wherein the hydrolysis step occurs after step i) and dehydration occurs simultaneously with ammoniation of the saturated hydroxylated fatty acid, for obtaining said unsaturated nitrile.

25. An unsaturated fatty nitrile, wherein it is obtained by a process as defined in claim 18.

26. The process of claim 6, wherein the acid catalyst is selected from the group consisting of sulfuric acid, phosphoric acid, sulfonic acids, alkyl sulfonates, and ion-exchange acid resins.

27. The process of claim 7, wherein the oxidative cleavage stage c) is carried out by using ozone in combination with oxygen.

28. The process of claim 7, wherein the catalyst comprises tungstic acid.

\* \* \* \* \*